United States Patent [19]

Lim et al.

[11] 4,255,411

[45] Mar. 10, 1981

[54] PROCESS OF DETERMINING AN IMMUNOGENIC SUBSTANCE BY COMPETITION WITH AN ANTIBODY IN A MICROCAPSULE

[75] Inventors: Franklin Lim, Richmond; Richard D. Moss, Chester, both of Va.

[73] Assignee: Damon Corporation, Needham Heights, Mass.

[21] Appl. No.: 963,932

[22] Filed: Nov. 27, 1978

Related U.S. Application Data

[63] Continuation-in-part of Ser. No. 606,166, Aug. 20, 1975.

[51] Int. Cl.$^3$ .................... A61K 43/00; G01N 33/48; G01T 1/00; B01J 13/00
[52] U.S. Cl. ..................................... 424/1; 23/230 B; 252/316; 424/12
[58] Field of Search ...................... 252/316; 23/230 B; 424/1, 12

[56] References Cited

U.S. PATENT DOCUMENTS

| | | | |
|---|---|---|---|
| 4,021,364 | 5/1977 | Speiser et al. | 424/1 |
| 4,115,534 | 9/1978 | Ithakissios | 252/316 |
| 4,131,544 | 12/1978 | Elahi | 23/230 B |
| 4,158,547 | 6/1979 | Rousseau et al. | 23/230 B |

*Primary Examiner*—Benjamin R. Padgett
*Assistant Examiner*—Christine M. Nucker

[57] ABSTRACT

A process for determining an immunogenic substance present in a sample wherein the immunogenic substance in the sample competes with a distinguishable analog of such substance for available binding sites on an antibody which is highly specific for the immunogenic substance in the sample. The antibody is encapsulated in a semipermeable microcapsule.

A specific example of the foregoing procedure is the determination of digoxin present in serum wherein the digoxin in the serum competes with radioiodine labeled digoxin for available binding sites on an antibody which is highly specific for digoxin and has been previously encapsulated in semi-permeable microcapsules. The concentration of digoxin in the sample is determined from a standard curve by relating digoxin concentration inversely to the percent of radioiodine labeled digoxin that is complexed to the antibody.

8 Claims, 3 Drawing Figures

PROCESS OF DETERMINING AN IMMUNOGENIC SUBSTANCE BY COMPETITION WITH AN ANTIBODY IN A MICROCAPSULE

CROSS REFERENCE TO A RELATED APPLICATION

This application is a continuation-in-part of U.S. patent application Ser. No. 606,166, filed Aug. 20, 1975 for Franklin Lim et al. entitled "Encapsulation of Labile Biological Material".

BACKGROUND OF THE INVENTION

A common known procedure for determining the amount of an antigen in a sample is to allow the antigen in the sample to compete with a distinguishable analog of the antigen for sites on an antibody which is highly specific for the antigen. This general method of determining the amount of antigen present is known as a competitive system. For example, if the amount of digoxin present in the serum is to be determined, an aliquot of the serum and an aliquot of radioactively labeled digoxin is allowed to react with an antibody specific for digoxin. The labeled and unlabeled digoxin compete for sites on the antibody. Thus, the greater the amount of digoxin in the sample, the lower will be the radioactive reading on the antibody.

Two common methods of performing such competitive determinations are known as "liquid phase radioimmunoassay" and "solid phase radioimmunoassay". In each system the immunogenic substance which is bound to an antibody must be removed from unbound immunogenic substance in order to make a measurement of the amount of labeled analog on the antibody. From this measurement, the amount of immunogenic substance in the sample is determined.

In "liquid" phase radioimmunoassay systems, the antibody, labeled analog and immunogenic substance to be determined are incubated in solution. A number of antibody binding sites are available and reaction time is rapid. To separate the antibody complexed immunogenic substance from the uncomplexed immunogenic substance, the antibody immunogenic complex is precipitated, centrifuged, and the supernatant is decanted.

"Solid phase" radioimmunoassay systems avoid the precipitation step. The antibody is bound to a glass chip or inside surface of a tube. Centrifugation of the glass chips or decantation of the coated tubes will separate the antibody complexed immunogenic substance from the uncomplexed immunogenic substance. However, the reaction time is relatively slow because the number of available active sites on the antibody is blocked by the chip or tube.

SUMMARY OF THE INVENTION

In accordance with the present invention, an immunogenic substance present in serum or other biological fluids is determined by allowing the immunogenic substance to compete with a distinguishable analog of such substance for sites on an antibody which is encapsulated in a semi-permeable microcapsule. The pores in the wall of the microcapsule are constructed such that the larger encapsulated molecules (the antibody) are trapped inside the capsule while smaller molecules (that is, the immunogenic substance) can diffuse freely in and out of the capsule. This procedure combines the inherent accuracy of a conventional liquid phase radioimmunoassay and the simplicity and convenience of a solid phase system.

In one specific embodiment of the invention, digoxin, present in the patient's serum, competes with labeled digoxin for available binding sites on an antibody which is highly specific for digoxin and which has been previously encapsulated in semipermeable nylon microcapsules. Antibody bound digoxin becomes trapped inside the capsule. Unbound digoxin is thus separated from bound digoxin by centrifugation. The concentration of digoxin in the sample is determined from a standard curve relating digoxin concentration to the percent of labeled digoxin bound to the antibody in the capsule. A standard curve is established using pure digoxin standards supplied in dilutions corresponding to levels below, within and above the therapeutic range.

The microcapsules used in this system are permeable to small molecular weight antigens, such as digoxin, and impermeable to large molecular weight substances such as digoxin antibodies. For quality control, the solution in the microcapsule is colored. A colored supernatant, after the capsules have settled out or sedimented via centrifugation, is indicative of microcapsule breakage and possible leakage of antibody.

The addition of patient serum or other source of digoxin initiates the reaction. Digoxin easily traverses the semipermeable microcapsules membrane and competes with added labeled digoxin at the digoxin-antibody binding sites.

The association of labeled digoxin on the digoxin-antibody is directly related to the amount of unlabeled digoxin passing into the microcapsule through pores in the semipermeable microcapsule wall. Unlike conventional assays, this assay avoids loss of clinical correlation with diagnosed conditions over a broad range of concentrations of protein, hormone, said interfering substances.

After incubation at 37° C. for 15 minutes (or at 20°-25° C. for 30 minutes), radioactively labeled digoxin is briefly counted for gamma radiation. With increased digoxin in the sample material, less radioactive digoxin will bind to antibody within the semipermeable microcapsule and the result will be lowered radioactivity of the capsule. This decrease in radioactivity may be correlated against a standard curve generated by known samples run simultaneously with the unknown sample. A direct reading of the results of the unknown sample against the standard curve will result in accurate assessment of the digoxin concentration of the sample.

Accordingly, it is an object of the invention to provide a competitive process for the determination of an immunogenic substance which combines the advantages of the solid phase radioimmunoassay system and the advantages of the liquid phase radioimmunoassay system.

A further object of the invention is to provide a highly reliable process for the determination of the amount of digoxin in serum.

DESCRIPTION OF THE PREFERRED EMBODIMENT

At the outset, the invention is described with respect to the determination of digoxin in which a direct radioimmunoassay of digoxin is performed. Semipermeable microcapsules are provided containing minute amounts of an antibody which is highly specific to digoxin trapped therein and a blue dye (to warn of capsule breakdown). An aliquot of the sample to be tested for digoxin concentration followed by an aliquot of radioactively labeled digoxin initiates the reaction. The digoxin of the sample, as well as the labeled digoxin rapidly traverse the microcapsule wall to enter the capsule to react with the antibody bound therein.

Within the capsule both labeled digoxin and digoxin from the sample compete for binding sites on the digoxin antibody that is found in solution within the capsule. An equilibrium proportional to the relative concentrations of labeled and unlabeled digoxin is reached after an incubation period. Typically, the incubation period at 37° C. is 15 minutes and at 20°-25° C. is 30 minutes.

After a first incubation, the capsules are washed in 20% polyethylene glycol 6000 solution in 0.5 M barbital buffer, pH 8.9 containing 0.15 M sodium chloride, followed by a final 5 minute incubation at 20°-25° C.

The microcapsule fraction is separated by centrifugation at 1400× g minimum for ten minutes at 20°-25° C. and the supernatant decanted.

Figure 2:
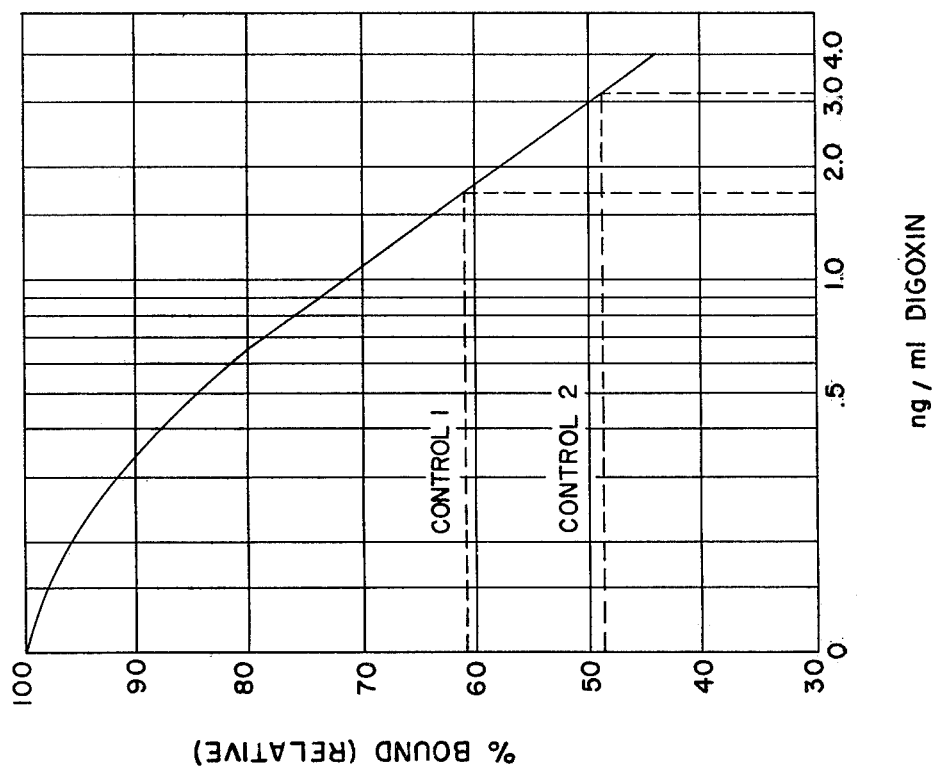
FIG. 2 shows digoxin as % bound (relative) vs. digoxin concentration. Percent bound (relative) is calculated as % bound (relative)=mean cpm bound/mean cpm bound of 0 ng/dl digoxin standard×100. [Data from Table I]
Figure 1:
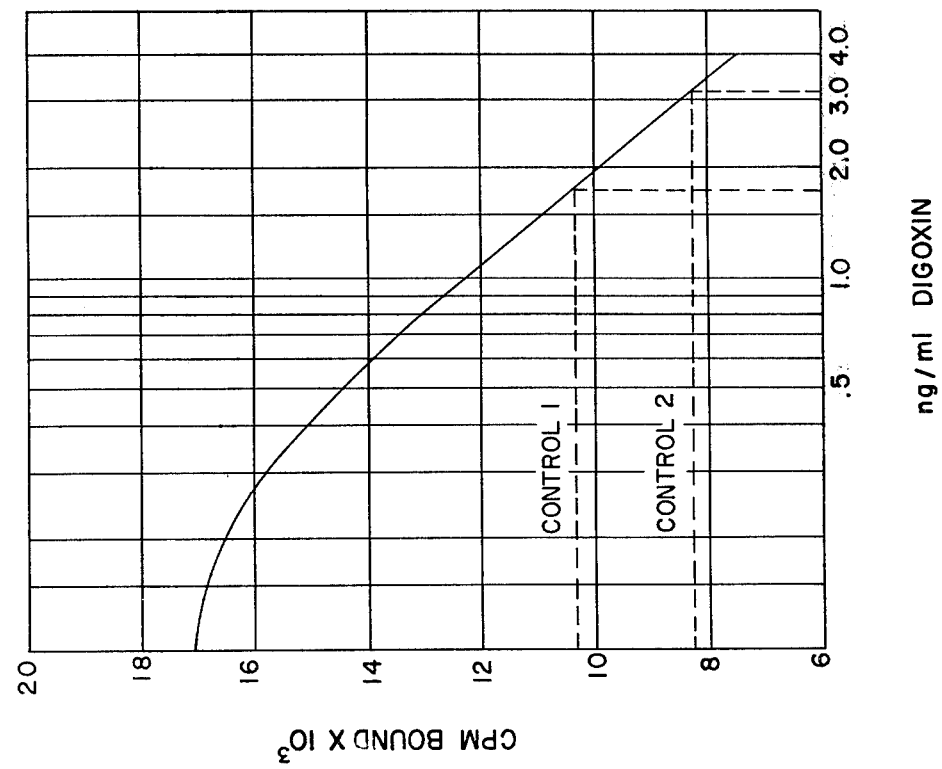
FIG. 1 shows the digoxin standard curve as counts per minute (cpm) bound to antibody as plotted on the linear scale against digoxin in nanograms/milliliter on the log scale of 2 cycle semilog paper with the data from Table I.

The microcapsule fraction is then counted for gamma emmission and a standard curve arrived at to which the test sample may be related for a direct measure of digoxin in weight per unit volume. FIG. 1 depicts such a curve compiled from the test results as shown in Table I. FIG. 2 employs the same data but expresses the digoxin in % bound where % bound=(cpm bound/mean cpm bound of 0 ng/ml digoxin standard)×100.

TABLE I

| | ng/ml | CPM Bound | |
|---|---|---|---|
| | Digoxin | 1 | 2 |
| Standards | 0 | 16,888 | 17,136 |
| | 0.5 | 14,464 | 14,473 |
| | 1.0 | 12,279 | 12,192 |
| | 2.0 | 9,690 | 9,717 |
| | 4.0 | 7,344 | 7,445 |
| Controls | 1 | 10,360 | 10,486 |
| | 2 | 8,226 | 8,380 |
| CPM Total = 26,780 | | | |

| Mean | Relative % Bound (CPM Bound/CPM Bound)* × 100 | Digoxin Value ng/ml |
|---|---|---|
| 17,012 | 100.0 | |
| 14,469 | 85.0 | |
| 12,236 | 72.0 | |
| 9,704 | 57.0 | |
| 7,395 | 43.0 | |
| 10,423 | 61.3 | 1.7 |
| 8,303 | 48.8 | 3.1 |

*Bound = CPM Bound at 0 ng/ml digoxin

The assay system of the instant process has been found to be quite precise. The intra assay variation is less than 7% and the interassay variation is less than 9%.

Intra Assay Variation

The coefficients of variation, CV, for two control samples, each assayed twenty-five (25) times within one experiment were found to be

| | Mean Digoxin ng/ml | CV |
|---|---|---|
| Control 1 | 1.54 | 4.9% |
| Control 2 | 2.95 | 6.2% |

InterAssay Variation

The coefficients of variation for two control samples, each assayed three times in eighteen separate experiments were found to be:

| | Mean Digoxin ng/ml | CV |
|---|---|---|
| Control 1 | 1.50 | 7.3% |
| Control 2 | 3.04 | 8.8% |

Table II shows the extremely high specificity of this assay for digoxin and to the exclusion of other potentially interfering substances.

TABLE II

Specificity
% Cross-reactivity of various biochemical compounds with microencapsulated antidigoxin antisera

| Compound | % Cross Reactivity |
|---|---|
| Digoxin | 100.00 |
| Digitoxin | 0.80 |
| Progesterone | 0.16 |
| Cortisol | 0.10 |
| Testosterone | 0.08 |
| Dehydroandrosterone sulfate | 0.08 |
| Cholesterol | 0.06 |
| Quabain | 0.02 |

Quantitative Recovery

The instant process has been found to be highly quantitative, reflecting no less than 96% recovery of the digoxin samples added.

TABLE III

Recovery Study

| Initial Digoxin Level ng/ml | Digoxin Added | Total Digoxin ng/ml | Measured Digoxin ng/ml | % Recovery |
|---|---|---|---|---|
| 0.64 | 0.5 | 1.14 | 1.13 | 99 |
| 0.64 | 1.0 | 1.64 | 1.72 | 105 |
| 0.64 | 2.0 | 2.64 | 2.70 | 102 |
| 0.64 | 4.0 | 4.64 | 4.45 | 96 |

It is of particular importance to note the high degree of correlation of the results of the instant process with digoxin determinations as made by other assay methods. Table IV compares the instant process with the assays of other commercially available test.

The systems A and C represent liquid assay systems with precipitating reagent separation while system B utilizes solid phase separation.

Table V expresses these comparative test results as showing a 0.97–0.98 correlation coefficient.

TABLE IV

| Sample No. | Present System | System A | System B | System C | Mean |
|---|---|---|---|---|---|
| 1 | 0.5 | 0.5 | 0.5 | 0.5 | 0.5 |
| 2 | 1.5 | 1.3 | 0.8 | 1.4 | 1.3 |
| 3 | 1.3 | 1.1 | 1.0 | 1.0 | 1.1 |
| 4 | 1.1 | 1.0 | 1.0 | 1.0 | 1.0 |
| 5 | 2.0 | 1.9 | 1.5 | 1.7 | 1.8 |
| 6 | 1.2 | 1.2 | 1.2 | 1.1 | 1.2 |
| 7 | 1.7 | 1.6 | 1.5 | 1.7 | 1.6 |
| 8 | 0.8 | 0.7 | 0.6 | 0.6 | 0.7 |
| 9 | 0.5 | 0.5 | 0.5 | 0.6 | 0.5 |
| 10 | 1.3 | 1.1 | 1.1 | 1.3 | 1.2 |
| 11 | 2.5 | 2.8 | 2.7 | 2.6 | 2.7 |
| 12 | 1.7 | 1.7 | 1.6 | 1.7 | 1.7 |
| 13 | 0.9 | 0.8 | 0.8 | 0.8 | 0.8 |
| 14 | 0.8 | 0.7 | 0.6 | 0.6 | 0.7 |
| 15 | 1.1 | 1.4 | 1.2 | 1.1 | 1.2 |
| 16 | 2.3 | 2.9 | 2.5 | 2.0 | 2.4 |
| 17 | 0.5 | 0.5 | 0.5 | 0.5 | 0.5 |
| 18 | 0.5 | 0.5 | 0.5 | 0.5 | 0.5 |
| 19 | 1.0 | 1.0 | 1.1 | 0.8 | 1.0 |
| 20 | 3.3 | 3.8 | 3.5 | 3.0 | 3.4 |
| 21 | 1.2 | 1.2 | 1.1 | 1.2 | 1.2 |
| 22 | 1.4 | 1.1 | 1.1 | 1.1 | 1.2 |
| 23 | 0.5 | 0.5 | 0.5 | 0.5 | 0.5 |
| 24 | 1.9 | 1.9 | 2.0 | 1.1 | 1.7 |
| 25 | 1.2 | 1.0 | 0.9 | 1.0 | 1.0 |
| 26 | 1.9 | 1.7 | 1.7 | 1.6 | 1.7 |
| 27 | 2.0 | 2.5 | 2.2 | 2.3 | 2.3 |
| 28 | 0.6 | 0.5 | 0.5 | 0.5 | 0.5 |
| 29 | 0.5 | 0.5 | 0.5 | 0.5 | 0.5 |
| 30 | 1.0 | 0.9 | 0.7 | 0.7 | 0.8 |
| 31 | 2.6 | 3.0 | 2.6 | 2.9 | 2.8 |
| 32 | 3.0 | 3.4 | 3.2 | 3.4 | 3.3 |
| 33 | 1.9 | 2.0 | 1.9 | 2.0 | 2.0 |
| 34 | 0.5 | 0.5 | 0.5 | 0.5 | 0.5 |
| 35 | 1.2 | 1.2 | 1.0 | 1.0 | 1.1 |
| 36 | 1.4 | 1.1 | 0.9 | 1.0 | 1.1 |
| 37 | 0.5 | 0.5 | 0.5 | 0.5 | 0.5 |
| 38 | 1.6 | 1.2 | 1.1 | 1.2 | 1.3 |
| 39 | 2.3 | 2.5 | 2.0 | 2.5 | 2.3 |
| 40 | 1.0 | 1.0 | 0.6 | 0.9 | 0.9 |
| 41 | 2.2 | 2.4 | 2.5 | 2.5 | 2.4 |
| 42 | 1.8 | 1.7 | 1.7 | 1.5 | 1.7 |
| 43 | 1.6 | 1.4 | 1.2 | 1.4 | 1.4 |
| 44 | 2.2 | 2.5 | 2.4 | 2.1 | 2.3 |
| 45 | 1.7 | 1.7 | 1.4 | 1.6 | 1.6 |
| 46 | 1.9 | 2.3 | 2.1 | 2.2 | 2.1 |
| 47 | 1.7 | 1.4 | 1.2 | 1.3 | 1.4 |
| 48 | 0.5 | 0.5 | 0.5 | 0.5 | 0.5 |
| 49 | 0.7 | 0.7 | 0.6 | 0.6 | 0.7 |
| 50 | 1.0 | 1.9 | 0.8 | 0.5 | 1.1 |
| 51 | 0.5 | 0.5 | 0.5 | 0.5 | 0.5 |
| 52 | 2.9 | 3.1 | 2.6 | 3.2 | 3.0 |
| 53 | 0.8 | 0.5 | 0.5 | 0.6 | 0.6 |
| 54 | 1.6 | 1.5 | 1.2 | 1.5 | 1.5 |
| 55 | 0.8 | 0.6 | 0.5 | 0.7 | 0.7 |
| 56 | 1.4 | 1.5 | 1.0 | 1.3 | 1.3 |
| 57 | 1.5 | 1.7 | 1.1 | 1.7 | 1.5 |
| 58 | 1.7 | 1.7 | 1.4 | 2.1 | 1.7 |
| 59 | 1.0 | 0.6 | 0.5 | 0.5 | 0.7 |
| 60 | 1.5 | 1.4 | 0.9 | 1.3 | 1.3 |
| 61 | 2.0 | 2.1 | 1.7 | 2.0 | 2.0 |
| 62 | 1.9 | 2.8 | 1.7 | 2.6 | 2.3 |
| 63 | 0.7 | 0.6 | 0.5 | 0.6 | 0.6 |
| 64 | 0.9 | 0.8 | 0.6 | 0.7 | 0.8 |
| 65 | 1.3 | 1.2 | 0.6 | 1.1 | 1.1 |
| 66 | 0.8 | 1.2 | 0.7 | 0.8 | 0.9 |
| 67 | 2.2 | 2.8 | 2.1 | 2.3 | 2.4 |
| 68 | 1.5 | 1.4 | 1.3 | 1.2 | 1.4 |
| 69 | 1.0 | 1.2 | 0.8 | 0.8 | 1.0 |
| 70 | 1.1 | 1.1 | 0.8 | 1.1 | 1.0 |
| 71 | 1.1 | 0.8 | 0.9 | 0.8 | 0.9 |
| 72 | 1.5 | 1.4 | 1.2 | 1.3 | 1.4 |
| 73 | 1.4 | 1.7 | 1.4 | 1.3 | 1.5 |
| 74 | 1.8 | 1.6 | 1.3 | 1.5 | 1.6 |
| 75 | 0.5 | 0.5 | 0.5 | 0.5 | 0.5 |
| 76 | 1.4 | 1.4 | 1.2 | 1.4 | 1.4 |
| 77 | 0.6 | 0.7 | 0.6 | 0.6 | 0.6 |
| 78 | 0.8 | 0.9 | 0.7 | 1.1 | 0.9 |
| 79 | 2.8 | 3.3 | 2.7 | 3.0 | 3.0 |
| 80 | 1.3 | 1.1 | 0.8 | 0.9 | 1.0 |
| 81 | 2.7 | 2.3 | 2.0 | 2.2 | 2.3 |
| 82 | 0.5 | 0.5 | 0.5 | 0.5 | 0.5 |
| 83 | 2.7 | 2.2 | 1.8 | 2.2 | 2.2 |
| 84 | 1.8 | 1.5 | 1.1 | 1.5 | 1.5 |
| 85 | 1.4 | 1.1 | 0.9 | 1.1 | 1.1 |
| 86 | 2.4 | 2.5 | 2.2 | 2.3 | 2.4 |
| 87 | 2.8 | 2.1 | 1.9 | 2.2 | 2.3 |
| 88 | 1.8 | 1.3 | 1.0 | 1.3 | 1.4 |
| 89 | 1.2 | 1.1 | 0.7 | 0.9 | 1.0 |
| 90 | 2.5 | 2.5 | 1.8 | 2.0 | 2.2 |
| 91 | 0.6 | 0.5 | 0.5 | 0.5 | 0.5 |
| 92 | 3.6 | 3.2 | 2.6 | 3.3 | 3.2 |
| 93 | 0.5 | 0.5 | 0.5 | 0.5 | 0.5 |
| 94 | 0.9 | 0.7 | 0.6 | 0.7 | 0.7 |
| 95 | 1.9 | 2.0 | 1.4 | 1.7 | 1.7 |
| 96 | 1.1 | 1.0 | 0.8 | 1.0 | 1.0 |
| 97 | 0.5 | 0.7 | 0.5 | 0.6 | 0.6 |
| 98 | 1.3 | 1.1 | 0.9 | 0.9 | 1.1 |
| 99 | 1.6 | 1.1 | 0.9 | 1.2 | 1.2 |
| 100 | 0.5 | 0.5 | 0.5 | 0.5 | 0.5 |
| 101 | 1.1 | 1.0 | 0.7 | 1.0 | 1.0 |
| 102 | 0.5 | 0.6 | 0.5 | 0.5 | 0.5 |
| 103 | 2.8 | 3.4 | 2.3 | 3.0 | 2.9 |
| 104 | 0.6 | 0.7 | 0.7 | 0.6 | 0.7 |
| 105 | 0.7 | 0.5 | 0.5 | 0.5 | 0.6 |
| 106 | 2.2 | 2.2 | 1.5 | 2.0 | 2.0 |
| 107 | 1.1 | 1.1 | 0.9 | 0.9 | 1.0 |
| 108 | 1.5 | 1.7 | 1.2 | 1.5 | 1.5 |
| 109 | 2.4 | 3.7 | 3.1 | 2.2 | 3.0 |
| 110 | 1.0 | 1.0 | 0.8 | 0.8 | 0.9 |
| 111 | 0.7 | 0.5 | 0.5 | 0.5 | 0.5 |
| 112 | 2.1 | 2.0 | 1.7 | 1.9 | 1.9 |
| 113 | 1.7 | 1.8 | 1.3 | 1.6 | 1.6 |
| 114 | 1.6 | 1.5 | 1.3 | 1.4 | 1.5 |
| 115 | 0.7 | 1.1 | 0.7 | 0.8 | 1.8 |
| 116 | 0.5 | 0.5 | 0.5 | 0.5 | 0.5 |
| 117 | 1.7 | 1.5 | 1.3 | 1.9 | 1.6 |
| 118 | 1.7 | 1.5 | 1.3 | 1.4 | 1.5 |
| 119 | 1.6 | 1.3 | 1.1 | 1.1 | 1.3 |
| 120 | 1.3 | 1.3 | 1.1 | 1.3 | 1.3 |
| 121 | 1.5 | 1.4 | 1.1 | 1.4 | 1.4 |
| 122 | 1.4 | 0.9 | 0.9 | 1.0 | 1.1 |
| 123 | 1.2 | 0.9 | 0.8 | 0.8 | 0.9 |
| 124 | 1.9 | 1.9 | 1.5 | 1.4 | 1.7 |
| 125 | 1.4 | 1.1 | 0.8 | 1.0 | 1.1 |
| 126 | 0.7 | 0.5 | 0.5 | 0.5 | 0.6 |
| 127 | 0.7 | 1.4 | 0.5 | 1.3 | 1.0 |
| 128 | 0.6 | 0.5 | 0.5 | 0.5 | 0.5 |
| 129 | 1.1 | 1.0 | 0.8 | 0.8 | 0.9 |
| 130 | 0.8 | 0.9 | 0.6 | 0.7 | 0.8 |
| 131 | 1.2 | 1.2 | 0.9 | 1.1 | 1.1 |
| 132 | 2.0 | 1.7 | 1.4 | 1.7 | 1.7 |
| 133 | 0.5 | 0.8 | 0.6 | 0.7 | 0.7 |
| 134 | 2.2 | 3.8 | 2.2 | 2.4 | 2.7 |
| 135 | 1.1 | 1.0 | 0.7 | 1.0 | 1.0 |

TABLE V

AGREEMENT FOR VARIOUS ASSAY PROCEDURES
Coefficients of correlation for 135 samples assayed by System A, System B, System C, and the Present System were:

| | n | r* | y |
|---|---|---|---|
| System A | 135 | 0.98 | 1.12 × −0.1 |
| System B | 135 | 0.97 | 0.90 × −0.02 |
| System C | 135 | 0.97 | 0.96 × +0 |
| Present System | 135 | 0.97 | 0.95 × +0.14 |

*r = coefficient of correlation

As one may see from this description, the procedure measures the concentration of digoxin in serum by means of a direct radioimmunoassay test system. Essentially, microencapsulated digoxin-antibody competively binds radioactive (125$_I$) labeled digoxin and digoxin, in a displacement reaction. In the presence of the standard, control, or patient specimen, the amount of radioactive digoxin bound to antibody is inversely proportional to the amount of digoxin in the sample being assayed. One of the unique features of microencapsulated antibody is the semipermeable nature of the microcapsule allows free passage of small molecules, such as digoxin easily and rapidly across the nylon membrane. Much larger serum protein molecules cannot pass through the microcapsule membrane nor may the digoxin-antibody diffuse out. A first requirement in performing the process of this invention is semipermeable microcapsules containing an active antibody or other large proteins which react specifically with the immunogenic substance to be determined.

In the above-disclosed process, these semipermeable microcapsules containing antibody are prepared according to the process described in Lim et al., "Encapsulation of Labile Biological Material", U.S. patent application Ser. No. 606,166, filed Aug. 20, 1975, the teachings of which are incorporated herein by reference. Pore size of such microcapsules should be sufficient to allow digoxin (MW=760) or other immunogenic substances to traverse the microcapsule membrane yet insufficient to permit exit of digoxin-antibody (MW>150,000) or other proteins specific to the immunogenic substance. Such microcapsules are prepared by Damon Diagnostics (115 Fourth Ave., Needham Heights, Mass. 02194).

A procedure for encapsulating antibody specific to digoxin is set forth below.

The components and their suppliers are listed below:

| | |
|---|---|
| Sodium Bicarbonate | |
| Cyclohexane | |
| Chloroform | All Fisher Chemical |
| Sodium Chloride | |
| Sodium Phosphate, monobasic | |
| Sodium Phosphate, dibasic | |
| 1,6-Hexanediamine | |
| Span-85 | |
| Tween-20 | Ruger Chemical, New Jersey |
| Anti-Digoxin Rabbit Antiserum | Arnel Products, Brooklyn, New York |
| Bovine Serum Albumin | |
| Comassie Brilliant Blue R | Sigma Chemical |
| Polyvinylpyrrolidone-40 | Aldrich Chemical |
| Terephthaloyl Chloride | Eastman Kodak |

The quantity of each ingredient is as follows:

| | |
|---|---|
| 1,6 Hexanediamine Carbonate | 30 ml |
| Phosphate Buffered Saline | 40 ml |
| Polyvinylpyrrolidone 40/Comassie Blue | 25 ml |
| Anti-Digoxin Rabbit Antiserum | 5 ml |
| Cyclohexane, ACS | 750 ml |
| SPAN-85 | 125 ml |
| Terephthaloyl Chloride Solution | 107.5 ml |
| Chloroform | 100 ml |
| Tween-20 Wash Solution Q.S. | 200 ml |
| Phosphate Buffered Saline Q.S. | 8 l |

Procedure: Rinse all glassware in distilled water prior to use.

1. Place 2 liter glass mixer in hood on magnetic stirrer.
2. On bench adjacent to hood, set up microscope.
3. In 250 ml glass graduated cylinder, carefully measure 125 ml SPAN-85.
4. Pour measured SPAN-85 into glass mixer in hood.
5. Measure 750 ml cyclohexane in a 1000 ml glass graduated cylinder. Pour into glass mixer in hood.
6. Place cover on mixer.
7. Turn on magnetic stirrer.
8. Measure: 30 ml Hexanedianmine Carbonate; 30 ml PBS; 25 ml 15% PVP/Comassie Blue/4% BSA; 5 ml Antibody; mix the 40 ml PBS with the 5 ml Antibody in a 50 graduated cylinder.
9. Put a 2-inch stir bar with spin ring in a 400 ml beaker. Place on magnetic stirrer.
10. To beaker add 30 ml hexanedianmine. Start magnetic stirrer.
11. To Hexanediamine in beaker add in the following specified order: 25 ml 15% PVP/Comassie Blue/4% BSA; 35 ml PBS/Antibody solution. Let mix for 2 min. Let solution mix for three (3) min.
12. While solution is mixing, measure one 70 ml portion and one 37.5 ml portion of TCL in separate 100 ml glass graduated cylinders. Cover with watch glass and set in hood. Measure four (4) 25 ml portions of chloroform in separate 25 ml glass graduated cylinders. Cover with watch glasses and set inside hood.
13. Through side arm of vial, add contents of 400 ml beaker to glass mixer in hood.
14. As rapidly as possible, with a disposable glass 1 ml pipette, take a sample of the solution in the mixer and put it on the microscope slide. Check to determine that the droplets are of an acceptable size. (10–80 microns in diameter)
15. When the droplets are of acceptable size T=0, add measured 70 ml of TCL through side arm of mixer. At T=30, exactly 30 seconds later, add second 37.5 ml portion of TCL to mixer through side arm. Let mix exactly 60 seconds.
16. At 60 seconds (T=90) add first 25 ml portion of chloroform. Mix 30 seconds. (T=120) Add second measured 25 ml chloroform, mix 30 seconds (T=150). Add third measured 25 ml chloroform. Mix 30 seconds (T=180). Add fourth measured 25 ml chloroform. Mix exactly 30 seconds (T=210"). Stop mixer.
17. Pour contents of mixer into two 1 liter plastic centrifuge bottles which have been rinsed in distilled water 3 times. Centrifuge at 500 RPM for three minutes.
18. Carefully decant supernatant.
19. To each bottle add approximately 50 ml of Tween-20 solution (i.e. approximately the same volume Tween-20 as capsules). Mix well with stir bar retriever for about 5 min.
20. Add approximately 10–15 mls PBS to each bottle. Stir well.
21. Repeat step 20 4–5 times.
22. Add 400 mls PBS. Mix well.
23. Balance and centrifuge bottles for 20 min. at 3000 RPM. Aspirate supernatant. Add approximately 800 ml PBS to each bottle. Stir well and cap.
24. Repeat step 23, 10 times. After final aspiration add 100 ml of PBS to each bottle and combine contents of both bottles. Shake well. Pour into 500 ml glass graduated cylinder and Q.S. to 500 ml with PBS.
25. Store in 1 liter glass reagent bottle at 4° C.

The Tween-20 wash solution is prepared as follows:
Procedure: Can be made day before use
1. Weigh 6.06 g sodium bicarbonate on triple beam balance.
2. Carefully put 6.06 g sodium bicarbonate into 250 ml volumetric flask containing stir bar.

3. Add approximately 200 ml purified water and stir on magnetic stirrer until sodium bicarbonate is dissolved.

4. Remove stir bar and Q.S. to 250 ml with purified water.

5. Carefully pour into 500 ml Erlenmeyer flask containing stir bar.

6. Carefully measure 250 ml Tween-20 in a 250 ml graduated cylinder.

7. Add to Erlenmeyer flask containing sodium bicarbonate solution.

8. Mix on magnetic stirrer until completely mixed (approximately 1 hour).

9. Store tightly sealed in polyethylene 1 L bottle with screw cap at approximately 25° C.

The terephthaloyl chloride solution is made as follows: Should be made day of use. DO NOT REFRIGERATE.

1. Weight of terephthaloyl chloride (TCI) is recorded on bottle containing TCI. Multiply weight of TCI in grams by ten to calculate volume in milliters cyclohexane/chloroform solution to add to TCI. p Calculations:

___g. TCI×10=___ml total volume cyclohexane/chloroform solution. Be sure total volume is sufficient for procedure being followed.

2. The cyclohexane/chloroform solution is four parts cyclohexane and, part chloroform. Divide the total volume cyclohexane/chloroform solution (Step 1 above) by five to calculate the volume chloroform. Multiply the chloroform volume by four to determine the cyclohexane volume.

Calculations:

(a) ___ml total volume−5=___ml chloroform. cyclohexane/chloroform (b) ___ml chloroform×4=___ml cyclohexane.

3. Carefully measure the calculated volumes cyclohexane and chloroform in graduated cylinders. Combine in Erlenmeyer flask. Swirl gently to mix. Cover with watch glass. Put in fume hood.

4. Put magnetic stirrer in fume hood.

5. Put bottle containing TCI on magnetic stirrer. Open bottle and as quickly as possible add a magnetic stir bar and cyclohexane/chloroform solution. Replace cap on bottle.

6. Stir on magnetic stirrer until all TCI is dissolved. It may be necessary to tip bottle to dissolve any TCI around top of bottle.

7. As quickly as possible, equally fill as many 200 ml glass centrifuge bottles as necessary with TCI solution and cap. Centrifuge 10 min. at 2600 rpm in room temperature centrifuge.

8. Pour supernatant in 500 ml amber bottles and seal well.

9. Store, tightly sealed, at approximately 25° C.

The procedure for preparing 15% PVP 40/Comassie Blue with 4% BSA is as follows:

Procedure: Make day of use. DO NOT REFRIGERATE.

1. Accurately weigh on triple beam balance 7.5 gm Polyvinylpyrrolidone 40; 2 g BSA; and 0.1 g (100 mg) Comassie Blue.

2. Put polyvinylpyrrolidone 40 into 50 ml glass beaker with stir bar. 3. Add approximately 20 ml PBS. Put glass cover plate on beaker.

4. Stir on magnetic stirrer until dissolved.

5. Put 0.1 g Comassie Blue and 2 g BSA into another 50 ml glass beaker.

6. Add approximately 20 ml PBS. Put glass cover plate on beaker.

7. Stir and heat slightly using magnetic hot plate/stirrer #10 with heating unit set on 2. Let stir until dissolved (aproximately 10 minutes).

8. Carefully add entire contents of beakers containing polyvinylpyrrolidone 40 solution and Comassie Blue solution to a 50 ml glass volumetric flask with stir bar.

9. Mix combined solutions for 10 minutes on magnetic stirrer. Remove stir bar.

10. Q.S. to 50 ml with PBS.

11. Adjust to pH=7.5±0.5 with 1 N sodium hydroxide. Orig. pH___final pH___Amt. 1N NaOH used ___.

12. Filter solution with Nalgene disposable membrane filter unit (0.45 u).

13. Store sealed in 60 ml polyethylene bottle with screw cap at approximately 25° C.

The procedure for preparing phosphate buffered saline is as follows:

Procedure: Can be made day before use.

1. In 1000 ml glass graduated cylinder, carefully measure 1000 ml phosphate buffered saline stock.

2. Pour into 20 L polyethylene carboy.

3. Measure, in 1000 ml glass graduated cylinder, 9000 ml deionized water and add to carboy containing phosphate buffered saline stock.

4. Stir using magnetic stir bar retriever.

5. Check pH. If necessary, adjust pH to 7.5±0.05. Final pH=___.

6. Store phosphate buffered saline in tightly sealed 20 liter polyethylene carboy. Store at approximately 25° C. until used.

The procedure for making 1,6 Hexanediamine Carbonate is as follows:

Procedure: Can be made day before use.

1. Place bottle of 1,6 hexanediamine in 3 liter beaker. Add enough tap water to the beaker to reach level of hexanediamine in bottle.

2. Loosen cap of hexanediamine bottle.

3. Place beaker on magnetic stirrer/hot plate with heat setting at 2 until hexanediamine is completely melted.

4. In graduated glass 25 ml cylinder, accurately measure 17.7 ml hexanediamine. Pour carefully into 500 ml amber bottle.

5. Accurately measure 32 ml purified water in 50 ml glass graduated cylinder. Add to hexanediamine in amber bottle.

6. Bubble $CO_2$ through solution for aproximately 1 hr. until pH=8.5±0.1. Final pH___.

7. Seal amber vial and store at aproximately 25° C.

Figure 3:
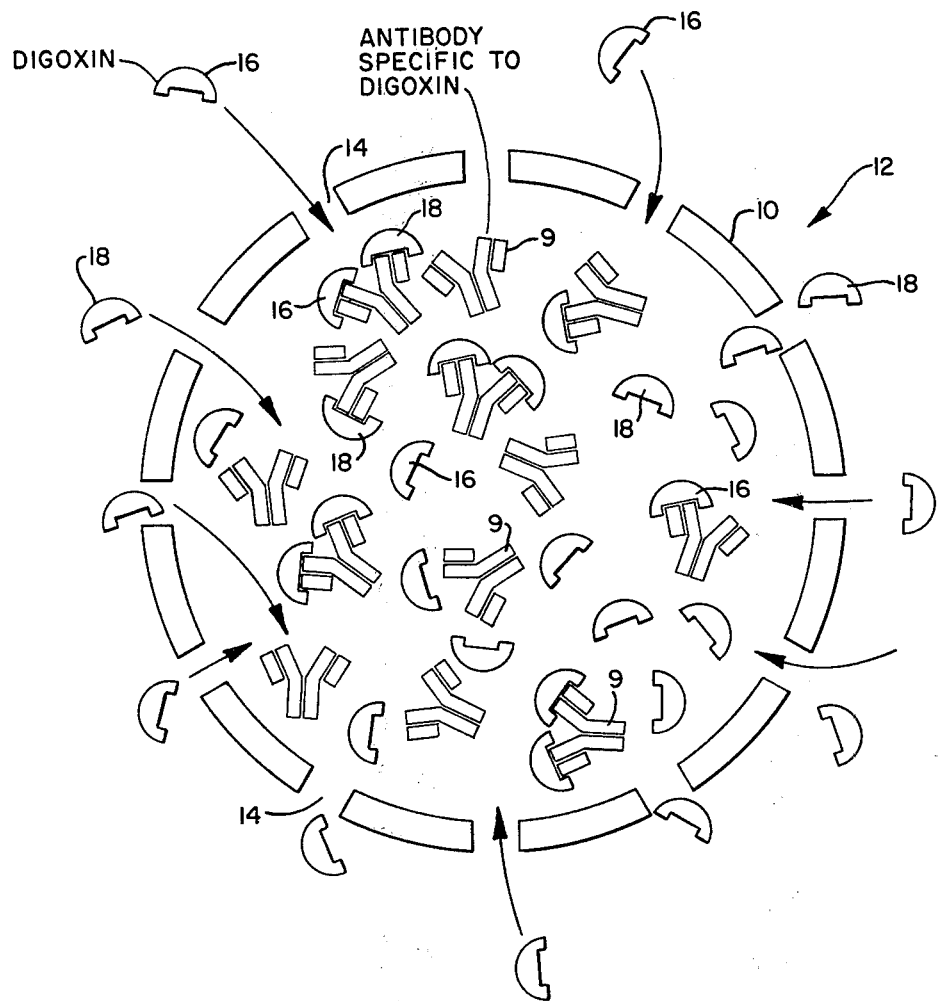
FIG. 3 is a diagram showing the retention of antibody and free passage of antigens in microcapsules formed in accordance with the present invention.

The microcapsule and principle of its operation are set forth diagramatically in FIG. 3. As is shown in FIG. 3, antibody 9 which is specific to digoxin is trapped within wall 10 of microcapsule 12. Walls 10 of the microcapsule 12, however, have openings 14 which are small enough to permit the free passage of digoxin. Thus, digoxin 16 from the sample and labeled digoxin 18 are free to pass through the walls of the microcapsules and compete with each other for sites on antibody 9. Any unbound digoxin 16 or 18 can be washed from within the microcapsule after incubation is completed.

As is set forth above, some of the digoxin is labeled and it is the labeled digoxin that competes with the unlabeled digoxin from the sample for sites on the antibody specific to digoxin. The preferred labeled digoxin is ($125_I$) digoxin which may be obtained from New England Nuclear Corporation, Billerica, Mass.

EXAMPLE 1

1. A sample or samples of serum to be tested is obtained through procedure well known to the art in this example controls are used.

2. Pipet 0.1 ml (100 μl) of each standard, control or unknown patient serum sample into correspondingly labeled tubes containing 0.5 ml of digoxin antibody microcapsule suspension as prepared above.

3. Pipet 0.5 (500 μl) of $125_I$ labeled digoxin (in phosphate-buffered saline) into each tube. Vortex for 3-4 seconds minimum.

4. Incubate all reaction tubes in a water bath (37° C.) for at least fifteen (15) minutes. [Alternatively incubate all reaction tubes at room temperature (20°-25° C.) for at least thirty (30) minutes.]

5. Add 0.5 ml (500 μl) of wash solution to each tube. Vortex for 3-4 seconds minimum.

6. Incubate all reaction tubes at room temperature (20°-25° C.) for five (5) minutes.

7. Centrifuge all tubes at 1600 xg minimum, for ten (10) minutes, room temperature (20°-25° C.), and decant supernatant into an appropriate waste container catching the last drop on blotter paper.

8. Count all tubes in a gamma counter, adjusted for $125_I$, for one (1) minute each.

9. Plot standard curve of known amounts of digoxin v. cpm and read unknown digoxin amounts from this curve.

Reagents Used

The digoxin-antibody is encapsulated in semi-permeable nylon microcapsules suspended in phosphate buffered saline as prepared above. For quality control, the antibody microcapsules contain blue dye (Comassie Blue $R_{250}$). A blue supernatant, after the microcapsules have settled out or sedimented via centrifugation, would be indicative of microcapsule breakage and possible antibody leakage.

$125_I$ Labeled Digoxin

Each ml of solution contains 10 μg of $125_I$ digoxin of less than 4.2 μCi.

Buffer Solution 0.015 M phosphate buffer, pH 7.5 containing 0.15 M sodium chloride 0.5% Bovine Serum Albumin (BSA), 0.1% sodium azide.

Wash Solution

Polyethylene glycol 6000, 20% solution in 0.5 M barbital buffer, pH 8.9 containing 0.15 M sodium chloride.

Calculation of the Results

The results of this experiment a typical test are shown in Table I and depicted graphically in FIGS. 1 and 2.

In FIG. 1 CPM is plotted on the linear scale of 2 cycle semilog graph paper against the concentration of digoxin in ng/ml (nanograms/milliliter) on the log scale. An alternative to plotting CPM vs. digoxin concentration is to plot % bound (relative) vs. digoxin concentration (see FIG. 2). This can be accomplished by calculating the % bound (relative) for each standard, control, or unknown, and plotting these values on two cycle semilog paper in a manner similar to that described previously for CPM. Percent bound (relative) is calculated as follows: % bound (relative)=(Mean CPM bound of 0 ng/ml digoxin standard)×100.

From the foregoing, it should be clear that the broad concept of the invention involves the encapsulation of a large molecule specific to the substance to be determined. The pores of the microcapsule are not large enough to permit passage of the encapsulated material. This encapsulated substance can be used to analyze any substance for which it is specific and which is small enough to pass through the pores in the capsule.

The invention may be embodied in other specific forms without departing from the spirit or essential characteristics thereof. The present embodiment and example is therefore to be considered in all aspects as illustrative, not restrictive, the scope of the invention being indicated by the appended claims rather than the foregoing description, and all changes which come within the meaning and range of equivalency of the claim therefore intended to be embraced therein.

We claim:

1. A process for measuring the concentration of an immunogenic substance in a sample, said process comprising the steps of:
   a. providing a microcapsule containing antibody to said substance, said microcapsule having walls of a permeability insufficient to allow traverse of said antibody but sufficient to allow passage of said substance and a distinguishable analog thereof;
   b. allowing the substance and a distinguishable analog thereof to traverse said semipermeable microcapsule wall to competitively bind onto the antibody contained within the semipermeable microcapsule;
   c. determining the relative binding of said substance and said distinguishable analog; and
   d. calculating from the determination of step c the amount of substance per unit volume of said sample by reference to a standard.

2. The process of claim 1 wherein the substance is digoxin.

3. The process of claim 2 wherein the distinguishable analog is radioactive digoxin.

4. The process of claim 2 wherein the distinguishable analog is ($125_I$) digoxin.

5. The process of claim 2 wherein the antibody is digoxin-antibody.

6. The process of claim 1 wherein the distinguishing property of the analog is radioactivity.

7. The process of claim 1 wherein said microcapsules contain a dye whereby breakage of the microcapsule is marked by escape of dye into said sample.

8. A material useful for the detection of digoxin comprising an antibody specific to digoxin encapsulated in a microcapsule having pores small enough to prevent the passage of the antibody but large enough to permit passage to digoxin into the microcapsule.

* * * * *